United States Patent [19]

Gericke et al.

[11] 4,153,693
[45] May 8, 1979

[54] 1,4-DIHYDRO-4-OXO-PYRIDYLACETAMIDO CEPHALOSPORINS AND THEIR UTILIZATION AS MEDICINAL AGENTS FOR COMBATING BACTERIAL INFECTIONS

[75] Inventors: Rolf Gericke; Werner Rogalski; Rolf Bergmann, all of Darmstadt; Walter Hameister, Berlin; Helmut Wahlig, Darmstadt, all of Fed. Rep. of Germany

[73] Assignee: Merck Patent Gesellschaft mit beschrankter Haftung, Darmstadt, Fed. Rep. of Germany

[21] Appl. No.: 503,705

[22] Filed: Sep. 6, 1974

[30] Foreign Application Priority Data

Sep. 8, 1973 [DE] Fed. Rep. of Germany ....... 2345402
Jun. 6, 1974 [DE] Fed. Rep. of Germany ....... 2427224

[51] Int. Cl.² .................. A61K 31/545; C07D 501/56; C07D 501/46
[52] U.S. Cl. ...................................... 424/246; 544/27; 544/28; 544/25
[58] Field of Search ............... 260/243 C; 544/27, 28, 544/25; 424/246

[56] References Cited

U.S. PATENT DOCUMENTS

| | | | |
|---|---|---|---|
| 3,218,318 | 11/1965 | Flynn | 260/243 C |
| 3,833,570 | 9/1974 | Holdrege | 260/243 C |
| 3,956,287 | 5/1976 | Bamburg et al. | 544/25 |
| 3,956,288 | 5/1976 | Bamburg et al. | 544/25 |
| 4,119,775 | 10/1978 | Bamburg et al. | 544/28 |

Primary Examiner—Donald G. Daus
Assistant Examiner—Diana G. Rivers
Attorney, Agent, or Firm—Millen & White

[57] ABSTRACT

Cephem derivatives of the formula

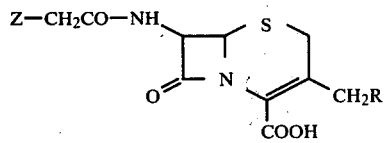

wherein Z is 1,4-dihydro-4-oxo-1-pyridyl or the corresponding group substituted by one or more of alkyl of 1-4 carbon atoms, alkoxy of 1-4 carbon atoms, OH, F, Cl, Br, I, $NO_2$ and $NH_2$; and R is H, —$OCOCH_3$ or -S-Het, wherein Het is 3-methyl-1,2,4-thiadiazolyl-5, 5-methyl-1,3,4-oxadiazolyl-2, 5-hydroxymethyl-1,3,4-oxadiazolyl-2, 5-methyl-1,3,4-thiadiazolyl-2, 5-hydroxymethyl-1,3,4-thiadiazolyl-2, tetrazolyl-5, 1-methyltetrazolyl-5, 1,2,3-triazolyl-4, 4-methyl-oxazolyl-2 or 1-oxidopyridinio-2, and the readily cleavable esters thereof and the physiologically acceptable salts thereof, possess anti-bacterial activity and can be prepared by reacting a 3-$CH_2$R-7-amino-3-cephem-4-carboxylic acid or a functional derivative thereof with a pyridone acetic acid of the formula Z-$CH_2$-COOH or a functional derivative thereof.

14 Claims, No Drawings

1,4-DIHYDRO-4-OXO-PYRIDYLACETAMIDO CEPHALOSPORINS AND THEIR UTILIZATION AS MEDICINAL AGENTS FOR COMBATING BACTERIAL INFECTIONS

BACKGROUND OF THE INVENTION

This invention relates to the novel cephem derivatives.

SUMMARY OF THE INVENTION

In a composition aspect, this invention relates to cephem derivatives of the general Formula 1

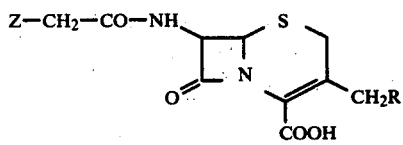

wherein Z is 1,4-dihydro-4-oxo-1-pyridyl or the corresponding group substituted by one or more of alkyl of 1–4 carbon atoms, alkoxy of 1–4 carbon atoms, OH, F, Cl, Br, I, $NO_2$ and $NH_2$; and R is H, —$OCOCH_3$ or —S—Het, wherein Het is 3-methyl-1,2,4-thiadiazolyl-5, 5-methyl-1,3,4-oxadiazolyl-2, 5-hydroxymethyl-1,3,4-oxadiazolyl-2, 5-methyl-1,3,4-thiadiazolyl-2, 5-hydroxymethyl-1,3,4-thiadiazolyl-2, tetrazolyl-5, 1-methyltetrazolyl-5, 1,2,3-triazolyl-4, 4-methyl-oxazolyl-2, or 1-oxidopyridinio-2; the readily cleavable esters of the 4-carboxylic acid group; and the physiologically acceptable salts thereof.

In another composition aspect, this invention relates to pharmaceutical compositions comprising a novel compound of this invention.

In a process aspect, this invention relates to processes for the production and for the use as antibacterial agents of the novel compounds of this invention.

DETAILED DISCUSSION

The novel compounds of this invention possess excellent antibacterial effectiveness against both gram-negative and against gram-positive bacteria. Compared with conventional cephalosporins obtained by a semi-synthetic method, the novel compounds exhibit marked differences with respect to the sensitivity of the individual germs. In numerous cases, known cephalosporins are considerably surpassed by the novel compounds of this invention, so that they have significant therapeutic advantages in combating specific bacterial infections. Thus, the minimum inhibitory concentration of 3-(1-methyltetrazolyl-5-mercaptomethyl)-7-(3,5-dibromo-1,4-dihydro-2-oxo-1-pyridylacetamido)-3-cephem-4-carboxylic acid and 3-(1-methyltetrazolyl-5-mercaptomethyl)-7-(3,5-dichloro-1,4-dihydro-4-oxo-1-pyridylacetamido)-3-cephem-4-carboxylic acid and the potassium salts of these acids, is lower by a factor of 2–8 compared to cephalothin and cephalexin for a number of pathogenic organisms, including *Escherichia coli, Salmonella typhimurium, Shigella krusea* and *Klebsiella pneumoniae*. In vivo, based on $ED_{50}$, these compounds and 7-(3,5-dichloro-1,4-dihydro-4-oxo-1-pyridylacetamido)-cephalosporanic acid, compared to cephalothin, were 1–20 times as effective in mice against *Staphylococcus aureus, Streptococcus pyogenes, Diplococcus pneumoniae, Salmonella newport, Klebsiella pneumoniae* and *Escherichia coli*. Furthermore, upon parenterial administration of the above-named compounds to dogs, serum concentrations were found comparable to those determined analogously for cephalothin and within 24 hours, 80–100% of the administered compound could be detected in the urine.

The compounds can, accordingly, be utilized as medicinal agents, particularly for combating bacterial infections. Furthermore, they can be employed as intermediates for the preparation of other drugs.

In the novel compounds of this invention, Z is preferably mono-, di- or tetrasubstituted, preferably disubstituted, 1,4-dihydro-4-oxo-1-pyridyl, but can also be the corresponding unsubstituted or trisubstituted substituent. The substituents on the Z group are, in case of mono-substitution, preferably in the 3-position; in case of disubstitution, in the 3- and 5-positions or in the 2- and 6-positions; and in case of trisubstitution in the 2-, 3- and 5-positions. Preferred substituents are Cl and Br, as well as OH, F, I, $NO_2$ and $NH_2$. An alkyl substituent is preferably methyl, but can also be ethyl, n-propyl, iso-propyl, n-butyl, iso-butyl, sec.-butyl and tert.-butyl. Alkoxy is preferably methoxy, but can also be ethoxy, n-propoxy, isopropoxy, n-butoxy, isobutoxy, sec.-butoxy and tert.-butoxy.

In addition to the unsubstituted 1,4-dihydro-2-oxo-1-pyridyl, Z can also be, e.g., 3,5-dichloro-, 3,5-dibromo-, as well as 3,5-difluoro-, 3,5-diiodo-, 3,5-dinitro-, 3,5-dihydroxy-, 3,5-dimethoxy-, 3,5-diamino-, 3-chloro-, 3-bromo-, 3-nitro-, 3-amino-, 3-hydroxy-, 3-methoxy-, 2,6-dimethyl-, 2,6-dimethyl-3,5-dichloro-, 2,6-dimethyl-3,5-dibromo-, 2,6-dimethyl-3,5-diiodo-, 3-chloro-5-nitro-, 3-bromo-5-nitro-, 3-chloro-5-amino-, 3-bromo-5-amino-, 3-chloro-5-hydroxy-, and 3-bromo-5-hydroxy-1,4-dihydro-4-oxo-1-pyridyl. Z can also be, for example, 3-fluoro-, 3-iodo-, 3-ethoxy-, 3-n-butoxy-, 3-methyl-, 3-ethyl-, 3-n-butyl-, 2,6-dimethyl-3-fluoro-, 2,6-dimethyl-3-chloro-, 2,6-dimethyl-3-bromo-, 2,6-dimethyl-3-iodo-, 2,6-dimethyl-3-hydroxy-, 2,6-dimethyl-3-nitro-, 2,6-dimethyl-3-amino-, 2,6-dimethyl-3-methoxy- and 2,6-dimethyl-3,5-difluoro-1,4-dihydro-4-oxo-1-pyridyl.

Of the compounds of Formula 1, preferred are those wherein R is —$OCOCH_3$, 1-methyltetrazolyl-5-mercapto or 5-methyl-1,3,4-thiadiazolyl-2-mercapto.

Esters of compounds of Formula 1 which can be split off are preferably the tert.-butyl esters as well as, for example, trimethylsilyl, benzyl, benzhydryl, trichloroethyl, benzoylmethyl, p-methoxybenzyl and methoxymethyl esters, and also the pivaloyloxymethyl esters.

In its process aspect, this invention relates to a process for the preparation of the compounds of Formula 1, esters thereof which are readily split off, and the physiologically acceptable salts thereof, which process comprises (a) reacting a 3-$CH_2$R-7-amino-3-cephem-4-carboxylic acid of Formula 2

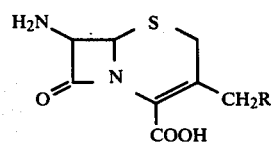

wherein R has the values given above, or a functional derivative thereof, with a pyridone acetic acid of the general formula Z—$CH_2COOH$ (3), wherein Z has the values given above, or a functional derivative thereof; or (b) reacting a 3-CH$_2$R-7-(X-acetamido)-3-cephem-4-carboxylic acid of general Formula 4

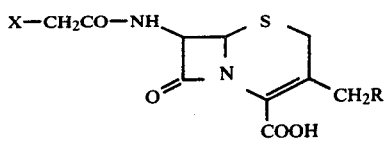

wherein X is Cl, Br or a reactively esterified OH-group, or a functional derivative thereof, with a pyridone of the general Formula Z-H (5) or a functional derivative thereof; or (c) liberating a functionally modified OH—, NH$_2$— or oxo- group contained in a compound otherwise corresponding to Formula 1 by treatment with solvolyzing or hydrogenolyzing agents; and optionally thereafter exchanging, in the thus-obtained compound, one or both substituents R and/or Z with another R and/or Z group by alkylating a hydroxy group by treatment with an alkylating agent, and/or by reducing a nitro group and/or an acetoxymethyl group by treatment with a reducing agent to an amino group or a methyl group, respectively, and/or by converting an acetoxy group into an —S-Het group by treatment with a thiol of the formula Het-SH or with a corresponding mercaptide, and/or by converting a carboxy group into a readily splittable carboxylic acid ester group by treatment with an esterification agent, and/or liberating the acid from a thus-obtained salt or ester and/or converting a thus-produced acidic or basic compound of Formula 1 into a physiologically acceptable salt thereof by treatment with a base or an acid, respectively.

All of these reactions take place according to methods known from the cephalosporin chemistry and described in detail in the literature.

The starting compounds for the process of this invention are either known or they can be produced according to conventional methods analogously to known compounds. For example, the acids of Formula 2 (R=—S—Het) are obtainable from 7-aminocephalosporanic acid (7-ACA; 2, R=—OCOCH$_3$) by reaction with the heterocyclic thiols of the formula HET—SH, which are known compounds for the most part, or with the associated metal mercaptides, e.g., by reaction of a corresponding alkali metal salt in hot aqueous acetone. The pyridone acetic acids of Formula 3 are obtainable from the pyridones of Formula 5 with chloracetic acid or bromacetic acid. The acids of Formula 4 are producible according to conventional methods, e.g., from the acids of Formula 2 with a substituted acetic acid of the formula X—CH$_2$COOH or a functional derivative thereof, e.g., chloracetyl chloride or bromacetyl bromide. The residue X is preferably bromine, but can also be Cl or a reactively esterified OH-group, especially alkylsulfonyloxy of 1-6 carbon atoms or arylsulfonyloxy of 6-10 carbon atoms, e.g., p-toluenesulfonyloxy. The substituted pyridones of Formula 5 are normally produced by the substitution of 4-pyridone.

Primarily suitable as functional derivatives of the acids of Formula 2 and Formula 4 are the readily splittable esters, e.g., the tert.-butyl esters, the trimethylsilyl esters (which are produced, for example, in situ from Formulae 2 or 4, respectively, and N-trimethylsilylacetamide), and the other above-named esters. Also suitable are the salts, particularly the neutral salts of these acids, especially the alkali metal (e.g., sodium, potassium), alkaline earth metal (e.g., magnesium, calcium), and ammonium salts. Among the latter, preferred are the salts derived from amines, especially from tertiary amines, e.g., triethylamine, triethanolamine, pyridine, collidine. These salts can be utilized as such in the reaction. It is also possible to produce these salts in situ from an acid of Formulae 2 or 4 and a base, e.g., NaHCO$_3$, Na$_2$HPO$_4$ or triethylamine.

Especially suitable as functional derivatives of the acids of Formula 3 are the halogenides, preferably the chlorides and bromides, and the anhydrides and mixed anhydrides, as well as the azides and activated esters, e.g., those with p-nitrophenol, 2,4-dinitrophenol, p-nitrophenylmercaptan, methylenecyanohydrin, or N-hydroxysuccinimide esters. Suitable as mixed anhydrides of the acids of Formula 3 are, for example, those of lower alkanoic acids, especially acetic acid and substituted acetic acids, e.g., trichloroacetic acid, pivalic acid and cyanoacetic acid, and anhydrides with carbonic acid monoesters which are obtainable, for example, by reaction of the acids of Formula 3 with benzyl chloroformate, p-nitrobenzyl chloroformate, isobutyl chloroformate, ethyl chloroformate or allyl chloroformate. All of these functional derivatives of acids of Formula 3 are preferably produced in situ.

Functional derivatives of the pyridones of Formula 5 are preferably the salts thereof, e.g., alkali metal, preferably, the Na and K salts, obtained, for example, by reaction with metallic Na or K in a high-boiling inert solvent, such as toluene or also under low-temperature condisitons with NaH.

In general, the reaction of the cephem derivatives of Formulae 2 and 4 (and the functional derivatives thereof) with the pyridone derivatives of Formulae 3 and 5, respectively (or a functional derivative thereof) is conducted in the presence of an inert solvent. Suitable as solvents are, in particular, chlorinated hydrocarbons, e.g., methylene chloride and chloroform; ether, e.g., diethyl ether, tetrahydrofuran and dioxane; ketones, e.g., acetone and butanone; amides, e.g., dimethylformamide (DMF), dimethylacetamide and hexamethylphosphoric triamide; sulfoxides, e.g., dimethyl sulfoxide (DMSO); water; and organic and aqueous inorganic bases, and mixtures of these solvents. If a salt of a compound of Formula 1 is to be prepared, an excess of the base serving for the production of this salt is particularly advantageous as the solvent, for example, triethylamine or aqueous sodium hydroxide solution.

The reaction of compounds of Formula 2 with those of Formula 3 and those of Formula 4 with those of Formula 5 (and the functional derivatives thereof) is normally conducted at temperatures of between −70° and +80°, preferably between −40° and +30°, especially between 0° and room temperature. The duration of the reaction is dependent on the type of starting materials employed and on the reaction temperature. Normally, the reaction time is between 5 minutes and 72 hours.

In detail, it is especially advantageous to react an ester, preferably a tert.-butyl ester, of an acid of Formula 2 with the free pyridone acetic acid of Formula 3. During this step, a water-binding agent is preferably added, for example, carbodiimides, especially dicyclohexylcarbodiimide (DCC). Thus, for example, 7-ACA-tert.-butyl ester, an acid of Formula 3, and DCC are reacted in approximately equimolar proportions and under cooling in an inert solvent, especially in methylene chloride, DMF, DMSO or also solvent mixtures.

The reaction of compounds of Formula 2 with functional derivatives of the acids of Formula 3 as well as the reaction of those of Formula 4 with those of Formula 5 are preferably conducted in an alkaline medium. Either the pyridone 5 is utilized in the form of a salt, e.g., an alkali metal salt, or a base is added to the reaction mixture, particularly $NaHCO_3$, $KHCO_3$, $Na_2CO_3$, $K_2CO_3$, NaOH, KOH, pyridine, or a base of low nucleophilicity, e.g., a tertiary amine, e.g., triethylamine, N-methylmorpholine, ethyl diisopropylamine, or potassium tert.-butylate.

The cephem derivatives of Formula 1 are also obtainable by liberating a functionally modified OH—, $NH_2$— or oxo-group in a compound otherwise corresponding to Formula 1, in accordance with conventional methods. The starting substances for this variation of the process are obtainable, for example, analogously to the above-described methods, but wherein sensitive functional groups are functionally modified during the synthesis by means of masking groups.

Examples of suitable functionally modified groups are: etherified or esterified hydroxy groups, e.g., benzyloxy or acetoxy; benzylated or acylated amino groups, e.g., benzylamino, benzyloxycarbamoyl, tert.-butoxycarbamoyl, acetylamino, wherein the especially preferred masking groups are those customary in the peptide chemistry. The oxo-group of the pyridone ring can be functionally modified in the form of a derivative of the corresponding enol form, for example in the form of a quaternary salt of general Formula 6,

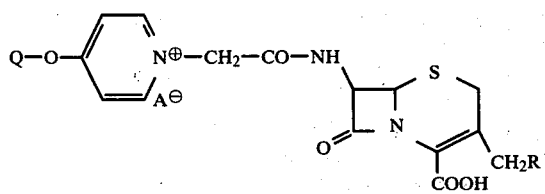

wherein Q represents a group removable by solvolysis, hydrogenolysis or catalysis, especially a readily splittable ether or ester group, and A is any desired anion, preferably chlorine or bromine, and the pyridine residue can be substituted in analogy to the group Z, as well as in the form of the readily splittable esters thereof. Suitable in particular are the corresponding benzyl and tert.-butyl ethers. In place of a compound of Formula 6, also suitable is a corresponding dipolar ion which can be produced from Formula 6 by splitting off HA.

The functionally modified groups can be liberated by solvolysis, especially hydrolysis or hydrogenolysis, in accordance with known methods disclosed in the literature. A solvolysis, preferably a hydrolysis, is effected, for example, with trifluoroacetic acid or with an aqueous mineral acid, e.g., hydrochloric acid, at a temperature of between −10° and 50°. A hydrogenolysis of functionally modified groups, especially a splitting off of benzyl and carbobenzoxy residues, takes place primarily by hydrogenation in the presence of noble metal catalysts, e.g., 5–50% strength palladium on carbon, or palladium oxide. Suitably, the hydrogenolysis is carried out at temperatures of between −10° and +50°, especially at room temperature, as well as at pressures of between 1 and 100 atmospheres, preferably under normal pressure. It is possible and frequently desirable to control the hydrogenolysis so that simultaneously further reductive changes occur in the molecule. For example, an acetoxymethyl group present in the 3-position can also be reduced to a methyl group.

If desired, an R substituent in the thus-obtained product of Formula 1 can be replaced by another R substituent and/or a Z substituent can be replaced by another Z substituent in accordance with methods known from the literature.

It is possible, for example, to alkylate a hydroxy group by treatment with an alkylating agent, e.g., with diazomethane, methyl bromide, methyl iodide, dimethyl or diethyl sulfate, ethyl, n-propyl, or n-butyl chloride, bromide or iodide.

It is also possible, for example, to reduce a nitro group on the pyridone ring to the amino group. Basically, all methods known per se, which are suitable for the reduction of nitro groups, can be utilized for this purpose, insofar as they do not cause undesirable changes in the molecule. Especially suitable is catalytic hydrogenation which can be effected, for example, with a noble metal catalyst, e.g., palladium, at room temperature and under normal pressure.

The reductive conversion of an acetoxymethyl group into a methyl group can likewise be accomplished by hydrogenation employing a noble metal catalyst, e.g., palladium, the reaction being advantageously conducted at low temperatures, i.e., room temperature, and somewhat elevated pressures, e.g., between 2 and 10 atmospheres.

If desired, several of the aforedescribed reductive conversions can also be achieved in a single step. Thus, it is possible to produce the corresponding desacetoxycephalosporanic acid (1, R=H) substituted by an amino group in the Z group by the hydrogenation of a cephalosporanic acid (1, R=$OCOCH_3$) substituted on the Z group by a nitro group.

It is also feasible to convert a thus-obtained cephalosporanic acid of Formula 1 (R=—$OCOCH_3$) into the corresponding thioether of Formula 1 (R=—S-Het) by reaction with a mercaptan of the formula Het-SH. Suitably, a salt of cephalosporanic acid is reacted with a salt of the thiol in aqueous acetone at temperatures of between 20° and 100° and pH values of between 4 and 8. Suitable as the salts are, in particular, the alkali metal salts, especially the sodium salts.

It is also possible to convert a free carboxylic acid of Formula 1 into a readily splittable carboxylic acid ester by means of esterification. For example, the tert.-butyl esters are produced by reacting the acids with isobutylene.

Conversely, an acid of Formula 1 can be liberated from a thus-produced salt or ester, for example by solvolysis, especially by acidic hydrolysis. The tert.-butyl esters, which are obtained especially advantageously during the synthesis, are split, for example, with trifluoroacetic acid at temperatures of between 0° and 40°.

The novel cephem derivatives are solid crystalline or amorphous products. They form solid and in many cases crystalline alkali metal, ammonium and alkaline earth metal salts, as well as salts with organic bases, e.g., diethylamine, triethylamine, diethanolamine, N-ethyldiethanolamine, pyrrolidine, piperidine, N-ethylpiperidine, 1-(2-hydroxyethyl)-piperidine, morpholine, procaine, benzylamine, dibenzylamine, 1-phenyl-2-propylamine, and further amines, as they are customarily employed for the production of cephalosporin salts.

Among the alkali metal salts, the sodium and potassium salts are of special significance. They can be produced by combining a solution of an acid of Formula 1 in an organic solvent with a solution of the sodium or potassium salt of a fatty acid, e.g., diethylacetic acid or 2-ethylcaproic acid, in a solvent, e.g., acetone or n-butanol, or in a mixture of solvents. The thus-produced salt which precipitates or which precipitates after the addition of ether, can be filtered off.

Basic compounds of Formula 1 can be converted into the associated acid addition salts thereof, e.g., into the hydrochlorides or citrates, in the usual manner by the use of an acid.

Since the compounds of Formula 1 do not have any sharply defined melting points, they are usually characterized by other physical data, advantageously by their infrared spectra. They show, in the infrared spectru, the absorption band of the β-lactam ring lying at 1760 to 1800 $cm^{-1}$. These compounds can also be characterized by their nuclear resonance spectra and by their thin-layer chromatogram. For this purpose, thin layer chromatography plates (Merck TLC instant plates silica gel $F_{254}$) can advantageously be utilized, using as eluent, for example, dioxane/water 85:15.

The novel compounds can be utilized in a mixture with solid, liquid and/or semiliquid excipients as medicinal agents in the human or veterinary medicine. Suitable vehicles are those organic or inorganic substances which are suitable for enteral, e.g., oral, but preferably for parenteral or topical application and which do not react with the novel compounds, e.g., water, vegetable oils, benzyl alcohols, polyethylene glycols, gelatin, lactose, amylose, magnesium stearate, talc, vaseline, cholesterol. Suitable for the enteral administration are, for example, tablets, capsules, dragees, syrups, elixirs, or suppositories. For parenteral application, advantageous are especially solutions, preferably oily or aqueous solutions, as well as suspensions, emulsions or implants, and for topical application, ointments, creams or powders. These preparations can be sterilized or mixed with auxiliary substances, emulsifiers, salts for influencing the osmotic pressure, buffers, coloring agents. They can also contain additional active agents.

The compounds of this invention are preferably administered like the known cephem derivatives, in doses of between 1 and 5000, especially between 200 and 2000 mg. per dosage unit, the exact dosage depending, in part, on the mode of administration, species of patient and bacterial infection, and can be determined by conventional techniques. The parenteral (e.g., intravenous or intramuscular) application is preferred.

Each of the compounds of Formula 1 set forth in the following examples is particularly suitable for the production of pharmaceutical preparations.

The IR spectra are recorded in KBr. DMF=dimethylformamide, 7-ACA=7-aminocephalosporanic acid, DCC=dicyclohexylcarbodiimide. The temperatures herein are in degrees Celsius.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE 1

(a) A solution of 12.5 g. of the tert.-butyl ester of 7-ACA and 8.9 g. of DCC in 100 ml. of methylene chloride/DMF 1:1 is cooled to 0°. The mixture is combined with 12.8 g. of 3,5-dibromo-4-pyridone-1-acetic acid; after 5 minutes, the ice bath is removed and the mixture agitated for another 30 minutes at 25°. The thus-formed urea is filtered off and the filtrate filtered over silica gel (eluent: ethyl acetate/1% methanol). The solvent is concentrated by evaporation, and the thus-obtained tert.-butyl ester of 7-(3,5-dibromo-1,4-dihydro-4-oxo-1-pyridylacetamido)-cephalosporanic acid is crystallized from ether.

(b) 22 g. of the tert.-butyl ester is dissolved in 30 ml. of trifluoroacetic acid. After 30 minutes, the solution is evaporated and the thus-produced 7-(3,5-dibromo-1,4-dihydro-4-oxo-1-pyridylacetamido)-cephalosporanic acid crystallized from ether.

IR: 1780, 1680, 1630, 1590, 1220 $cm^{-1}$.

Analogously, using 7-ACA with
4-pyridone-1-acetic acid
2,6-dimethyl-4-pyridone-1-acetic acid
3-methoxy-4-pyridone-1-acetic acid
3-n-butoxy-4-pyridone-1-acetic acid
3-hydroxy-4-pyridone-1-acetic acid
3-fluoro-4-pyridone-1-acetic acid
3-chloro-4-pyridone-1-acetic acid
3-bromo-4-pyridone-1-acetic acid
3-iodo-4-pyridone-1-acetic acid
3,5-difluoro-4-pyridone-1-acetic acid
3,5-dichloro-4-pyridone-1-acetic acid
3,5-diiodo-4-pyridone-1-acetic acid
2,6-dimethyl-3,5-dichloro-4-pyridone-1-acetic acid
2,6-dimethyl-3,5-dibromo-4-pyridone-1-acetic acid
2,6-dimethyl-3,5-diiodo-4-pyridone-1-acetic acid
3-nitro-4-pyridone-1-acetic acid
3,5-dinitro-4-pyridone-1-acetic acid
3-chloro-5-nitro-4-pyridone-1-acetic acid
3-bromo-5-nitro-4-pyridone-1-acetic acid
3-chloro-5-amino-4-pyridone-1-acetic acid
3-bromo-5-amino-4-pyridone-1-acetic acid
3-methyl-5-chloro-4-pyridone-1-acetic acid
3-methyl-5-bromo-4-pyridone-1-acetic acid
3-chloro-5-hydroxy-4-pyridone-1-acetic acid
3-bromo-5-hydroxy-4-pyridone-1-acetic acid
3-bromo-5-chloro-4-pyridone-1-acetic acid
3-bromo-5-fluoro-4-pyridone-1-acetic acid and
3-chloro-5-fluoro-4-pyridone-1-acetic acid,
the following final products are obtained by way of the corresponding tertiary butyl esters:
7-(1,4-dihydro-4-oxo-1-pyridylacetamido)-cephalosporanic acid
7-(2,6-dimethyl-1,4-dihydro-4-oxo-1-pyridylacetamido)-cephalosporanic acid
7-(3-methoxy-1,4-dihydro-4-oxo-1-pyridylacetamido)-cephalosporanic acid
7-(3-n-butoxy-1,4-dihydro-4-oxo-1-pyridylacetamido)-cephalosporanic acid
7-(3-hydroxy-1,4-dihydro-4-oxo-1-pyridylacetamido)-cephalosporanic acid
7-(3-fluoro-1,4-dihydro-4-oxo-1-pyridylacetamido)-cephalosporanic acid
7-(3-chloro-1,4-dihydro-4-oxo-1-pyridylacetamido)-cephalosporanic acid
7-(3-bromo-1,4-dihydro-4-oxo-1-pyridylacetamido)-cephalosporanic acid 7-(3-iodo-1,4-dihydro-4-oxo-1-pyridylacetamido)-cephalosporanic acid 7-(3,5-difluoro-1,4-dihydro-4-oxo-1-pyridylacetamido)-cephalosporanic acid 7-(3,5-dichloro-1,4-dihydro-4-oxo-1-pyridylacetamido)-cephalosporanic acid,
IR: 1760, 1730, 1700, 1670, 1600, 1390, 1220 cm$^{-1}$;

7-(3,5-diiodo-1,4-dihydro-4-oxo-1-pyridylacetamido)-cephalosporanic acid, potassium salt,
IR: 1770, 1620, 1580, 1290, 1240 cm$^{-1}$;

7-(2,6-dimethyl-3,5-dichloro-1,4-dihydro-4-oxo-1-pyridylacetamido)-cephalosporanic acid 7-(2,6-dimethyl-3,5-dibromo-1,4-dihydro-4-oxo-1-pyridylacetamido)-cephalosporanic acid 7-(2,6-dimethyl-3,5-diiodo-1,4-dihydro-4-oxo-1-pyridylacetamido)-cephalosporanic acid 7-(3-nitro-1,4-dihydro-4-oxo-1-pyridylacetamido)-cephalosporanic acid 7-(3,5-dinitro-1,4-dihydro-4-oxo-1-pyridylacetamido)-cephalosporanic acid, potassium salt,
IR: 1780, 1730, 1680, 1620, 1520, 1330, 1230 cm$^{-1}$;

7-(3-chloro-5-nitro-1,4-dihydro-4-oxo-1-pyridylacetamido)-cephalosporanic acid 7-(3-bromo-5-nitro-1,4-dihydro-4-oxo-1-pyridylacetamido)-cephalosporanic acid 7-(3-chloro-5-amino-1,4-dihydro-4-oxo-1-pyridylacetamido)-cephalosporanic acid 7-(3-bromo-5-amino-1,4-dihydro-4-oxo-1-pyridylacetamido)-cephalosporanic acid 7-(3-methyl-5-chloro-1,4-dihydro-4-oxo-1-pyridylacetamido)-cephalosporanic acid 7-(3-methyl-5-bromo-1,4-dihydro-4-oxo-1-pyridylacetamido)-cephalosporanic acid 7-(3-chloro-5-hydroxy-1,4-dihydro-4-oxo-1-pyridylacetamido)-cephalosporanic acid 7-(3-bromo-5-hydroxy-1,4-dihydro-4-oxo-1-pyridylacetamido)-cephalosporanic acid 7-(3-bromo-5-chloro-1,4-dihydro-4-oxo-1-pyridylacetamido)-cephalosporanic acid 7-(3-bromo-5-fluoro-1,4-dihydro-4-oxo-1-pyridylacetamido)-cephalosporanic acid and 7-(3-chloro-5-fluoro-1,4-dihydro-4-oxo-1-pyridylacetamido)-cephalosporanic acid, respectively.

(c) 6.78 g. of the thus-obtained 7-(3,5-dibromo-1,4-dihydro-4-oxo-1-pyridylacetamido)-cephalosporanic acid is dissolved in 60 ml. of saturated aqueous sodium bicarbonate solution at a pH of below 7 and combined with 1.2 g. of 1-methyltetrazole-5-thiol in 20 ml. of acetone. The reaction solution is agitated for 2 hours at 80° and at a pH of 6.3 under a nitrogen atmosphere. The acetone is thereupon removed, the solution is washed with ether and acidified to pH 2. The thus-obtained 3-(1-methyltetrazolyl-5-mercaptomethyl)-7-(3,5-dibromo-1,4-dihydro-4-oxo-1-pyridylacetamido)-3-cephem-4-carboxylic acid is filtered off and dried. Potassium salt, IR: 1765, 1630, 1600, 1390, 1360, 1220 cm$^{-1}$.

Analogously, the following compounds are obtained from the corresponding cephalosporanic acids:

3-(1-methyltetrazolyl-5-mercaptomethyl)-7-(1,4-dihydro-4-oxo-1-pyridylacetamido)-3-cephem-4-carboxylic acid 3-(1-methyltetrazolyl-5-mercaptomethyl)-7-(2,6-dimethyl-1,4-dihydro-4-oxo-1-pyridylacetamido)-3-cephem-4-carboxylic acid 3-(1-methyltetrazolyl-5-mercaptomethyl)-7-(3-methoxy-1,4-dihydro-4-oxo-1-pyridylacetamido)-3-cephem-4-carboxylic acid 3-(1-methyltetrazolyl-5-mercaptomethyl)-7-(3-n-butoxy-1,4-dihydro-4-oxo-1-pyridylacetamido)-3-cephem-4-carboxylic acid 3-(1-methyltetrazolyl-5-mercaptomethyl)-7-(3-hydroxy-1,4-dihydro-4-oxo-1-pyridylacetamido)-3-cephem-4-carboxylic acid 3-(1-methyltetrazolyl-5-mercaptomethyl)-7-(3-fluoro-1,4-dihydro-4-oxo-1-pyridylacetamido)-3-cephem-4-carboxylic acid 3-(1-methyltetrazolyl-5-mercaptomethyl)-7-(3-chloro-1,4-dihydro-4-oxo-1-pyridylacetamido)-3-cephem-4-carboxylic acid 3-(1-methyltetrazolyl-5-mercaptomethyl)-7-(3-bromo-1,4-dihydro-4-oxo-1-pyridylacetamido)-3-cephem-4-carboxylic acid 3-(1-methyltetrazolyl-5-mercaptomethyl)-7-(3-iodo-1,4-dihydro-4-oxo-1-pyridylacetamido)-3-cephem-4-carboxylic acid 3-(1-methyltetrazolyl-5-mercaptomethyl)-7-(3,5-difluoro-1,4-dihydro-4-oxo-1-pyridylacetamido)-3-cephem-4-carboxylic acid 3-(1-methyltetrazolyl-5-mercaptomethyl)-7-(3,5-dichloro-1,4-dihydro-4-oxo-1-pyridylacetamido)-3-cephem-4-carboxylic acid, potassium salt,
IR: 1770, 1690, 1630, 1590, 1220 cm$^{-1}$;

3-(1-methyltetrazolyl-5-mercaptomethyl)-7-(3,5-diiodo-1,4-dihydro-4-oxo-1-pyridylacetamido)-3-cephem-4-carboxylic acid, K salt,
IR: 1760, 1660, 1610, 1570, 1390, 1360, 1210 cm$^{-1}$;

3-(1-methyltetrazolyl-5-mercaptomethyl)-7-(2,6-dimethyl-3,5-dichloro-1,4-dihydro-4-oxo-1-pyridylacetamido)-3-cephem-4-carboxylic acid 3-(1-methyltetrazolyl-5-mercaptomethyl)-7-(2,6-dimethyl-3,5-dibromo-1,4-dihydro-4-oxo-1-pyridylacetamido)-3-cephem-4-carboxylic acid 3-(1-methyltetrazolyl-5-mercaptomethyl)-7-(2,6-dimethyl-3,5-diiodo-1,4-dihydro-4-oxo-1-pyridylacetamido)-3-cephem-4-carboxylic acid 3-(1-methyltetrazolyl-5-mercaptomethyl)-7-(3-nitro-1,4-dihydro-4-oxo-1-pyridylacetamido)-3-cephem-4-carboxylic acid 3-(1-methyltetrazolyl-5-mercaptomethyl)-7-(3,5-dinitro-1,4-dihydro-4-oxo-1-pyridylacetamido)-3-cephem-4-carboxylic acid 3-(1-methyltetrazolyl-5-mercaptomethyl)-7-(3-chloro-5-nitro-1,4-dihydro-4-oxo-1-pyridylacetamido)-3-cephem-4-carboxylic acid 3-(1-methyltetrazolyl-5-mercaptomethyl)-7-(3-bromo-5-nitro-1,4-dihydro-4-oxo-1-pyridylacetamido)-3-cephem-4-carboxylic acid 3-(1-methyltetrazolyl-5-mercaptomethyl)-7-(3-chloro-5-amino-1,4-dihydro-4-oxo-1-pyridylacetamido)-3-cephem-4-carboxylic acid 3-(1-methyltetrazolyl-5-mercaptomethyl)-7-(3-bromo-5-amino-1,4-dihydro-4-oxo-1-pyridylacetamido)-3-cephem-4-carboxylic acid 3-(1-methyltetrazolyl-5-mercaptomethyl)-7-(3-chloro-5-hydroxy-1,4-dihydro-4-oxo-1-pyridylacetamido)-3-cephem-4-carboxylic acid 3-(1-methyltetrazolyl-5-mercaptomethyl)-7-(3-bromo-5-hydroxy-1,4-dihydro-4-oxo-1-pyridylacetamido)-3-cephem-4-carboxylic acid 3-(1-methyltetrazolyl-5-mercaptomethyl)-7-(3-bromo-5-chloro-1,4-dihydro-4-oxo-1-pyridylacetamido)-3-cephem-4-carboxylic acid.

Analogously, using the following starting compounds:
3-methyl-1,2,4-thiadiazole-5-thiol
5-methyl-1,3,4-oxadiazole-2-thiol
5-hydroxymethyl-1,3,4-oxadiazole-2-thiol
5-methyl-1,3,4-thiadiazole-2-thiol
5-hydroxymethyl-1,3,4-thiadiazole-2-thiol
tetrazole-5-thiol
1,2,3-triazole-4-thiol
4-methyloxazole-2-thiol and
2-mercaptopyridine-N-oxide,
the following products are produced from the corresponding cephalosporanic acids:
3-(3-methyl-1,2,4-thiadiazolyl-5-mercaptomethyl)-7-(3,5-dichloro-1,4-dihydro-4-oxo-1-pyridylacetamido)-3-cephem-4-carboxylic acid, potassium salt;
3-(3-methyl-1,2,4-thiadiazolyl-5-mercaptomethyl)-7-(3,5-dibromo-1,4-dihydro-4-oxo-1-pyridylacetamido)-3-cephem-4-carboxylic acid, potassium salt;
3-(3-methyl-1,2,4-thiadiazolyl-5-mercaptomethyl)-7-(3,5-diiodo-1,4-dihydro-4-oxo-1-pyridylacetamido)-3-cephem-4-carboxylic acid;
3-(3-methyl-1,2,4-thiadiazolyl-5-mercaptomethyl)-7-(3-bromo-5-nitro-1,4-dihydro-4-oxo-1-pyridylacetamido)-3-cephem-4-carboxylic acid, sodium salt,
IR: 1770, 1700, 1650, 1620, 1530, 1370, 1335, 1300, 1235 cm$^{-1}$;
3-(3-methyl-1,2,4-thiadiazolyl-5-mercaptomethyl)-7-(3-chloro-5-nitro-1,4-dihydro-4-oxo-1-pyridylacetamido)-3-cephem-4-carboxylic acid, sodium salt,
IR: 1765, 1655, 1615, 1365, 1330, 1290, 1230 cm$^{-1}$;
3-(3-methyl-1,2,4-thiadiazolyl-5-mercaptomethyl)-7-(3-bromo-5-amino-1,4-dihydro-4-oxo-1-pyridylacetamido)-3-cephem-4-carboxylic acid;
3-(3-methyl-1,2,4-thiadiazolyl-5-mercaptomethyl)-7-(3-chloro-5-amino-1,4-dihydro-4-oxo-1-pyridylacetamido)-3-cephem-4-carboxylic acid;
3-(3-methyl-1,2,4-thiadiazolyl-5-mercaptomethyl)-7-(3-bromo-5-hydroxy-1,4-dihydro-4-oxo-1-pyridylacetamido)-3-cephem-4-carboxylic acid;
3-(3-methyl-1,2,4-thiadiazolyl-5-mercaptomethyl)-7-(3-chloro-5-hydroxy-1,4-dihydro-4-oxo-1-pyridylacetamido)-3-cephem-4-carboxylic acid;
3-(3-methyl-1,2,4-thiadiazolyl-5-mercaptomethyl)-7-(3-bromo-5-chloro-1,4-dihydro-4-oxo-1-pyridylacetamido)-3-cephem-4-carboxylic acid;
3-(5-methyl-1,3,4-oxadiazolyl-2-mercaptomethyl)-7-(3,5-dichloro-1,4-dihydro-4-oxo-1-pyridylacetamido)-3-cephem-4-carboxylic acid, potassium salt,
IR: 1755, 1675, 1580, 1470, 1380, 1345, 1210 cm$^{-1}$;
3-(5-methyl-1,3,4-oxadiazolyl-2-mercaptomethyl)-7-(3,5-dibromo-1,4-dihydro-4-oxo-1-pyridylacetamido)-3-cephem-4-carboxylic acid, potassium salt,
IR: 1760, 1680, 1620, 1590, 1380, 1350, 1210 cm$^{-1}$;
3-(5-methyl-1,3,4-oxadiazolyl-2-mercaptomethyl)-7-(3,5-diiodo-1,4-dihydro-4-oxo-1-pyridylacetamido)-3-cephem-4-carboxylic acid, potassium salt,
IR: 1760, 1675, 1605, 1345, 1200 cm$^{-1}$;
3-(5-hyroxymethyl-1,3,4-oxadiazolyl-2-mercaptomethyl)-7-(3,5-dichloro-1,4-dihydro-4-oxo-1-pyridylacetamido)-3-cephem-4-carboxylic acid;
3-(5-hydroxymethyl-1,3,4-oxadiazolyl-2-mercaptomethyl)-7-(3,5-dibromo-1,4-dihydro-4-oxo-1-pyridylacetamido)-3-cephem-4-carboxylic acid;
3-(5-hydroxymethyl-1,3,4-oxadiazolyl-2-mercaptomethyl)-7-(3,5-diiodo-1,4-dihydro-4-oxo-1-pyridylacetamido)-3-cephem-4-carboxylic acid;
3-(5-methyl-1,3,4-thiadiazolyl-2-mercaptomethyl)-7-(3,5-dichloro-1,4-dihydro-4-oxo-1-pyridylacetamido)-3-cephem-4-carboxylic acid,
IR: 1770, 1690, 1640, 1590, 1380, 1220 cm$^{-1}$;
3-(5-methyl-1,3,4-thiadiazolyl-2-mercaptomethyl)-7-(3,5-dibromo-1,4-dihydro-4-oxo-1-pyridylacetamido)-3-cephem-4-carboxylic acid, potassium salt,
IR: 1760, 1690, 1620, 1590, 1390, 1360, 1220 cm$^{-1}$;
3-(5-methyl-1,3,4-thiadiazolyl-2-mercaptomethyl)-7-(3,5-diiodo-1,4-dihydro-4-oxo-1-pyridylacetamido)-3-cephem-4-carboxylic acid;
3-(5-methyl-1,3,4-thiadiazolyl-2-mercaptomethyl)-7-(3-bromo-5-nitro-1,4-dihydro-4-oxo-1-pyridylacetamido)-3-cephem-4-carboxylic acid, sodium salt,
IR: 1770, 1695, 1650, 1620, 1375, 1330, 1230 cm$^{-1}$;
3-(5-methyl-1,3,4-thiadiazolyl-2-mercaptomethyl)-7-(3-chloro-5-nitro-1,4-dihydro-4-oxo-1-pyridylacetamido)-3-cephem-4-carboxylic acid, sodium salt,
IR: 1765, 1660, 1620, 1385, 1330, 1235 cm$^{-1}$;
3-(5-methyl-1,3,4-thiadiazolyl-2-mercaptomethyl)-7-(3-bromo-5-amino-1,4-dihydro-4-oxo-1-pyridylacetamido)-3-cephem-4-carboxylic acid;
3-(5-methyl-1,3,4-thiadiazolyl-2-mercaptomethyl)-7-(3-chloro-5-amino-1,4-dihydro-4-oxo-1-pyridylacetamido)-3-cephem-4-carboxylic acid;
3-(5-methyl-1,3,4-thiadiazolyl-2-mercaptomethyl)-7-(3-bromo-5-hydroxy-1,4-dihydro-4-oxo-1-pyridylacetamido)-3-cephem-4-carboxylic acid;
3-(5-methyl-1,3,4-thiadiazolyl-2-mercaptomethyl)-7-(3-chloro-5-hydroxy-1,4-dihydro-4-oxo-1-pyridylacetamido)-3-cephem-4-carboxylic acid;
3-(5-methyl-1,3,4-thiadiazolyl-2-mercaptomethyl)-7-(3-bromo-5-chloro-1,4-dihydro-4-oxo-1-pyridylacetamido)-3-cephem-4-carboxylic acid;
3-(5-hydroxymethyl-1,3,4-thiadiazolyl-2-mercaptomethyl)-7-(3,5-dichloro-1,4-dihydro-4-oxo-1-pyridylacetamido)-3-cephem-4-carboxylic acid;
3-(5-hydroxymethyl-1,3,4-thiadiazolyl-2-mercaptomethyl)-7-(3,5-dibromo-1,4-dihydro-4-oxo-1-pyridylacetamido)-3-cephem-4-carboxylic acid;
3-(5-hydroxymethyl-1,3,4-thiadiazolyl-2-mercaptomethyl)-7-(3,5-diiodo-1,4-dihydro-4-oxo-1-pyridylacetamido)-3-cephem-4-carboxylic acid;
3-(tetrazolyl-5-mercaptomethyl)-7-(3,5-dichloro-1,4-dihydro-4-oxo-1-pyridylacetamido)-3-cephem-4-carboxylic acid, potassium salt,
IR: 1760, 1630, 1590, 1220 cm$^{-1}$;
3-(tetrazolyl-5-mercaptomethyl)-7-(3,5-dibromo-1,4-dihydro-4-oxo-1-pyridylacetamido)-3-cephem-4-carboxylic acid, potassium salt,
IR: 1760, 1630, 1590, 1220 cm$^{-1}$;
3-(tetrazolyl-5-mercaptomethyl)-7-(3,5-diiodo-1,4-dihydro-4-oxo-1-pyridylacetamico)-3-cephem-4-carboxylic acid, potassium salt;
3-(1,2,3-triazolyl-4-mercaptomethyl)-7-(3,5-dichloro-1,4-dihydro-4-oxo-1-pyridylacetamido)-3-cephem-4-carboxylic acid, potassium salt,
IR: 1760, 1680, 1630, 1590, 1360, 1220 cm$^{-1}$;

3-(1,2,3-triazolyl-4-mercaptomethyl)-7-(3,5-dibromo-1,4-dihydro-4-oxo-1-pyridylacetamido)-3-cephem-4-carboxylic acid, potassium salt,
IR: 1760, 1620, 1590, 1390, 1360, 1220 cm$^{-1}$;

3-(1,2,3-triazolyl-4-mercaptomethyl)-7-(3,5-diiodo-1,4-dihydro-4-oxo-1-pyridylacetamido)-3-cephem-4-carboxylic acid, potassium salt,
IR: 1760, 1670, 1620, 1360, 1220 cm$^{-1}$;

3-(4-methyloxazolyl-2-mercaptomethyl)-7-(3,5-dichloro-1,4-dihydro-4-oxo-1-pyridylacetamido)-3-cephem-4-carboxylic acid, potassium salt;

3-(4-methyloxazolyl-2-mercaptomethyl)-7-(3,5-dibromo-1,4-dihydro-4-oxo-1-pyridylacetamido)-3-cephem-4-carboxylic acid, potassium salt;

3-(4-methyloxazolyl-2-mercaptomethyl)-7-(3,5-diiodo-1,4-dihydro-4-oxo-1-pyridylacetamido)-3-cephem-4-carboxylic acid;

3-(1-oxidopyridinio-2-mercaptomethyl)-7-(3,5-dichloro-1,4-dihydro-4-oxo-1-pyridylacetamido)-3-cephem-4-carboxylic acid;

3-(1-oxidopyridinio-2-mercaptomethyl)-7-(3,5-dibromo-1,4-dihydro-4-oxo-1-pyridylacetamido)-3-cephem-4-carboxylic acid, potassium salt,
IR: 1760, 1680, 1620, 1580, 1470, 1350, 1220 cm$^{-1}$; and 3-(1-oxidopyridinio-2-mercaptomethyl)-7-(3,5-diiodo-1,4-dihydro-4-oxo-1-pyridylacetamido)-3-cephem-3-carboxylic acid.

EXAMPLE 2

28 mg. of the tert.-butyl ester of 7-aminodesacetoxycephalosporanic acid (obtainable from the acid and isobutylene in dioxane/H$_2$SO$_4$ at 25°), 59 mg. of 3,5-diiodo-4-pyridone-1-acetic acid, and 38 mg. of DCC are dissolved under ice cooling in 2 ml. of absolute methylene chloride and agitated for 2 hours at 25°. The reaction mixture is purified over silica gel with ethyl acetate/methanol, the eluate is concentrated by evaporation and crystallized with ether, thus obtaining the tert.-butyl ester of 7-(3,5-diiodo-1,4-dihydro-4-oxo-1-pyridylacetamido)-desacetoxycephalosporanic acid. Free acid, potassium salt, IR: 1760, 1670, 1600, 1400, 1360, 1210 cm$^{-1}$.

Analogously, the following products are obtained with the corresponding pyridone acetic acids:

7-(3,5-dichloro-1,4-dihydro-4-oxo-1-pyridylacetamido)-desacetoxycephalosporanic acid, and 7-(3,5-dibromo-1,4-dihydro-4-oxo-1-pyridylacetamido)-desacetoxycephalosporanic acid.

EXAMPLE 3

(a) 297 mg. of 3-nitro-4-pyridone-1-acetic acid, 328 mg. of 7-ACA tert.-butyl ester, and 312 mg. of DCC are dissolved in 3 ml. of dimethyl sulfoxide and agitated for 7 minutes at 25°. The reaction mixture is poured into 100 ml. of water, the thus-obtained precipitate is filtered, taken up as much as possible in methylene chloride, and filtered over silica gel. After evaporation, the tert.-butyl ester of 7-(3-nitro-1,4-dihydro-4-oxo-1-pyridylacetamido)-cephalosporanic acid is obtained; IR: 1790, 1730, 1710, 1660, 1610, 1520, 1380, 1330, 1240, 1160 cm$^{-1}$. Free acid, IR: 3300, 1770, 1710, 1680, 1660, 1590, 1560, 1330, 1250, 1230 cm$^{-1}$.

(b) 200 mg. of the tert.-butyl ester is taken up in 60 ml. of methanol and hydrogenated with the addition of 200 mg. of 5% Pd-carbon for 15 minutes at 25° and under normal pressure. The catalyst is filtered off, the solution is evaporated, and the residue is recrystallized with the use of ether, thus obtaining the tert.-butyl ester of 7-(3-amino-1,4-dihydro-4-oxo-1-pyridylacetamido)-cephalosporanic acid. Free acid, IR: 3350, 1780, 1670, 1540, 1390, 1240, 1080, 1040 cm$^{-1}$.

EXAMPLE 4

Under ice cooling, 0.224 ml. of trichloroacetyl chloride is added to 443 mg. of 3,5-dichloro-4-pyridone-1-acetic acid in 10 ml. of absolute DMF. After 30 minutes of agitation, a solution of 554 mg. of 7-ACA and 1 g. of N-trimethylsilylacetamide in 5 ml. of DMF is added thereto. The mixture is agitated for 30 minutes under ice cooling, then poured into water, and adjusted to pH 5. The mixture is washed with ether, a pH of 2 is set, and the mixture is extracted with ethyl acetate, dried, evaporated, and crystallized with ether, thus producing 7-(3,5-dichloro-1,4-dihydro-4-oxo-1-pyridylacetamido)-cephalosporanic acid.

EXAMPLE 5

0.224 ml. of trichloroacetyl chloride is added to 443 mg. of 3,5-dichloro-4-pyridone-1-acetic acid in 5 ml. of absolute DMF. After 30 minutes of agitation, a solution of 554 mg. of 7-ACA and 0.84 ml. of triethylamine in 20 ml. of methylene chloride are added thereto. The mixture is stirred for 30 minutes, then poured into water and adjusted to pH 6. The mixture is washed with methylene chloride, and worked up as usual, thus producing 7-(3,5-dichloro-1,4-dihydro-4-oxo-1-pyridylacetamido)-cephalosporanic acid.

EXAMPLE 6

A solution of 272 mg. of 7-ACA and 1 ml. of triethylamine in 10 ml. of methylene chloride is combined at 0° in incremental portions under agitation with 336 mg. of 3,5-dibromo-1,4-dihydro-4-oxo-1-pyridylacetazide. The mixture is stirred for 1 hour, filtered, and the product is 7-(3,5-dibromo-1,4-dihydro-4-oxo-1-pyridylacetamido)-cephalosporanic acid.

EXAMPLE 7

10 g. of 7-ACA is suspended in 95 ml. of absolute methylene chloride; the mixture is cooled to −10° and dissolved under agitation in 12.9 ml. of triethylamine; the solution is agitated for 45 minutes at −30°. Thereafter, a freshly prepared solution of 3,5-dichloro-4-pyridone-1-acetyl chloride (obtained by adding 2.68 ml. of thionyl chloride dropwise to a solution of 8.12 g. of 3,5-dichloro-4-pyridone-1-acetic acid in 40 ml. of DMF at −40°) is added dropwise to this mixture at a temperature of below −20°. The mixture is agitated for 45 minutes at −20°, then allowed to warm up to 0°, and repeatedly extracted with sodium bicarbonate solution. The separated aqueous phases are acidified with hydrochloric acid and extracted with tetrahydrofuran/ethyl acetate. The organic phases are dried over sodium sulfate and evaporated, thus obtaining 7-(3,5-dichloro-1,4-dihydro-4-oxo-1-pyridylacetamido)-cephalosporanic acid.

EXAMPLE 8

(a) A solution of 95 mg. of 4-pyridone in 3 ml. of absolute DMF is combined with 24 mg. of NaH. The mixture is cooled with ice, 495 mg. of the tert.-butyl ester of 7-bromoacetamidocephalosporanic acid is added thereto, and the mixture is allowed to reach room temperature and poured into 60 ml. of water. The solution is washed with ether and extracted with methylene chloride. The extract is dried and, with ether, the tert.-butyl ester of 7-(1,4-dihydro-4-oxo-1-pyridylacetamido)-cephalosporanic acid is precipitated.

IR: 1780, 1730, 1640, 1560, 1260, 1240, 1160 cm$^{-1}$.

(b) 200 mg. of the tert.-butyl ester is dissolved in 3 ml. of trifluoroacetic acid. After allowing the mixture to stand for one-half hour, it is evaporated, dissolved in a small amount of methanol, and precipitated with ether. The product is 7-(1,4-dihydro-4-oxo-1-pyridylacetamido)-cephalosporanic acid.

Analogously, the corresponding cephalosporanic acids are obtained by way of the corresponding tert.-butyl esters employing the following compounds:
2,6-dimethyl-4-pyridone
3-methoxy-4-pyridone
3-n-butoxy-4-pyridone
3-hydroxy-4-pyridone
3-fluoro-4-pyridone
3-chloro-4-pyridone
3-bromo-4-pyridone
3-iodo-4-pyridone
3,5-difluoro-4-pyridone
(obtainable from 4-pyridone and CF$_3$OF)
3,5-dichloro-4-pyridone
3,5-dibromo-4-pyridone
3,5-diiodo-4-pyridone
2,6-dimethyl-3,5-dichloro-4-pyridone
2,6-dimethyl-3,5-dibromo-4-pyridone
2,6-dimethyl-3,5-diiodo-4-pyridone
3-nitro-4-pyridone
3,5-dinitro-4-pyridone
3-chloro-5-nitro-4-pyridone
3-bromo-5-nitro-4-pyridone.

(c) 150 mg. of the acid is dissolved in a small amount of methanol, mixed with methanolic diethylacetic acid potassium salt solution, and precipitated with ether, thus obtaining the associated potassium salt.

(d) A solution of 407 mg. of 7-(1,4-dihydro-4-oxo-1-pyridylacetamido)-cephalosporanic acid and 500 mg. of ammonium bicarbonate in 5 ml. of water is hydrogenated on 30 mg. of palladium oxide hydrate at 0° and 3.5 atmospheres. After working up the reaction mixture as usual, 7-(1,4-dihydro-4-oxo-1-pyridylacetamido)-desacetoxycephalosporanic acid is obtained.

EXAMPLE 9

A solution of 535 mg. of the tert.-butyl ester of 7-(3-benzylamino-1,4-dihydro-4-oxo-1-pyridylacetamido)-cephalosporanic acid (obtainable from 3-benzylamino-1,4-dihydro-4-oxo-1-pyridylacetic acid and 7-ACA tert.-butyl ester) in 100 ml. of methanol is hydrogenated on 300 mg. of 5% Pd-carbon at 25° and normal pressure until the absorption of hydrogen has ceased. The reaction product is filtered and evaporated, thus obtaining the tert.-butyl ester of 7-(3-amino-1,4-dihydro-4-oxo-1-pyridylacetamido)-cephalosporanic acid.

The active compounds of Formula 1 can be processed into pharmaceutical preparations in accordance with methods known from the literature, as demonstrated by the following example:

EXAMPLE A

Ampoules:

1 kg. of the potassium salt of 7-(3,5-dichloro-1,4-dihydro-4-oxo-1-pyridylacetamido)-cephalosporanic acid is dissolved in 3 l. of bidistilled water, filtered under sterile conditions, filled into ampoules, lyophilized aseptically, and sealed under sterilization. Each ampoule contains 1 g. of active agent.

The solution ampoules are obtained by dissolving 50 g. of lidocaine hydrochloride in 3 l. of twice-distilled water and, after sterile filtration, filling the solution into ampoules which are sterilized for 20 minutes at 120°. Each solution ampoule contains 50 mg. of lidocaine hydrochloride in 3 ml. of water.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

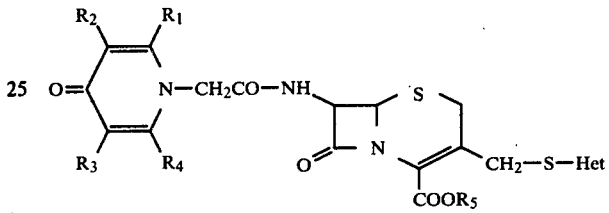

wherein R$_1$, R$_2$, R$_3$ and R$_4$ each are selected from the group consisting of hydrogen, alkyl of 1–4 carbon atoms, alkoxy of 1–4 carbon atoms, OH, F, Cl, Br, I, NO$_2$ and NH$_2$; Het is 3-methyl-1,2,4-thiadiazolyl-5, 5-methyl-1,3,4-oxadiazolyl-2, 5-hydroxymethyl-1,3,4-oxadiazolyl-2, 5-methyl-1,3,4-thiadiazolyl-2, 5-hydroxymethyl-1,3,4-thiadiazolyl-2, tetrazolyl-5, 1-methyltetrazolyl-5, 1,2,3-triazolyl-4, 4-methyloxazolyl-2 and 1-oxidopyridinio-2; and R$_5$ is selected from the group consisting of hydrogen, tert.-butyl, trimethylsilyl, benzyl, benzhydryl, trichloroethyl, benzoylmethyl, p-methoxybenzyl, methoxymethyl and pivaloyloxymethyl; and the physiologically acceptable salts thereof.

2. A compound of the formula

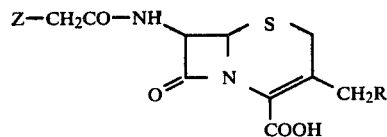

wherein Z is 3,5-dihalo-1,4-dihydro-4-oxo-1-pyridyl and R is —S—Het, wherein Het is 3-methyl-1,2,4-thiadiazolyl-5, 5-methyl-1,3,4-oxadiazolyl-2, 5-hydroxymethyl-1,3,4-oxadiazolyl-2, 5-methyl-1,3,4-thiadiazolyl-2, 5-hydroxymethyl-1,3,4-thiadiazolyl-2, tetrazolyl-5, 1-methyltetrazolyl-5, 1,2,3-triazolyl-4, 4-methyloxazolyl-2 or 1-oxidopyridinio-2, a corresponding ester of the 4-carboxylic acid group selected from the group consisting of tert.-butyl, trimethylsilyl, benzyl, benzhydryl, trichloroethyl, benzoylmethyl, p-methoxybenzyl, methoxymethyl and pivaloyloxymethyl esters, or a physiologically acceptable salt thereof.

3. A 4-carboxylic acid of claim 2 or an alkali metal salt thereof wherein Z is 3,5-dichloro- or 3,5-dibromo-1,4-dihydro-4-oxo-1-pyridyl.

4. A compound of claim 3 wherein R is 5-methyl-1,3,4-thiadiazolyl-2-mercapto.

5. A compound of claim 3 wherein R is 1-methyltetrazolyl-5-mercapto.

6. A compound of claim 2, 3-(1-methyltetrazolyl-5-mercaptomethyl)-7-(3,5-dichloro-1,4-dihydro-4-oxo-1-pyridylacetamido)-3-cephem-4-carboxylic acid or an alkali metal salt thereof.

7. A compound of claim 2, 3-(1-methyltetrazolyl-5-mercaptomethyl)-7-(3,5-dibromo-1,4-dihydro-4-oxo-1-pyridylacetamido)-3-cephem-4-carboxylic acid or an alkali metal salt thereof.

8. A compound of claim 2, 3-(5-methyl-1,3,4-thiadiazolyl-2-mercaptomethyl)-7-(3,5-dichloro-1,4-dihydro-4-oxo-1-pyridylacetamido)-3-cephem-4-carboxylic acid or an alkali metal salt thereof.

9. A compound of claim 2, 3-(5-methyl-1,3,4-thiadiazolyl-2-mercaptomethyl)-7-(3,5-dibromo-1,4-dihydro-4-oxo-1-pyridylacetamido)-3-cephem-4-carboxylic acid or an alkali metal salt thereof.

10. A compound of claim 1, 3-(1-methyltetrazolyl-5-mercaptomethyl)-7-(3-chloro-5-amino-1,4-dihydro-4-oxo-1-pyridylacetamido)-3-cephem-4-carboxylic acid.

11. A compound of claim 1, 3-(1-methyltetrazolyl-5-mercaptomethyl)-7-(3-bromo-5-amino-1,4-dihydro-4-oxo-1-pyridylacetamido)-3-cephem-4-carboxylic acid.

12. A pharmaceutical composition comprising an anti-bacterially effective amount per unit dosage of a compound of claim 1, in admixture with a pharmaceutically acceptable carrier.

13. A method of treating bacterial infections in mammals which comprises administering to an infected mammal an anti-bacterially effective amount of a compound of claim 1.

14. A pharmaceutical composition comprising an anti-bacterially effective amount per unit dosage of a compound of claim 2 in admixture with a pharmaceutically acceptable carrier.

* * * * *